United States Patent [19]

Onopchenko et al.

[11] Patent Number: 4,474,989

[45] Date of Patent: Oct. 2, 1984

[54] PROCESS FOR PREPARING DINITROBENZOPHENONES

[75] Inventors: Anatoli Onopchenko, Monroeville; Edward T. Sabourin, Allison Park; Charles M. Selwitz, Monroeville, all of Pa.

[73] Assignee: Gulf Research & Development Company, Pittsburgh, Pa.

[21] Appl. No.: 394,261

[22] Filed: Jul. 1, 1982

[51] Int. Cl.$^3$ .................. C07C 45/00; C07C 49/786
[52] U.S. Cl. .................. 568/306; 528/353; 564/423; 585/446; 585/451; 585/459; 585/461
[58] Field of Search ............ 568/306; 585/446, 451, 585/459, 461; 528/353

[56] References Cited

U.S. PATENT DOCUMENTS

| | | | |
|---|---|---|---|
| 3,280,200 | 10/1966 | Greer | 568/306 |
| 3,452,047 | 6/1969 | Frye | 568/306 |
| 3,542,862 | 11/1970 | Chemerda et al. | 568/306 |
| 3,641,132 | 2/1972 | Schulz et al. | 568/306 |
| 3,721,713 | 3/1973 | Bloom | 568/306 |

*Primary Examiner*—Natalie Trousof
*Assistant Examiner*—Vera C. Clarke
*Attorney, Agent, or Firm*—Deane E. Keith; Forrest D. Stine

[57] ABSTRACT

A process for preparing dinitrobenzophenones which comprises reacting benzene with ethylene in the presence of an alkylation catalyst to obtain an alkylation product containing unreacted benzene, ethylbenzene, polyethylbenzenes, 1,1-diphenylethane and heavier products, separating benzene, ethylbenzene and polyethylbenzenes from said alkylation product, recovering from the remainder of said alkylation product a fraction whose boiling points fall within the temperature range of about 260° to about 290° C., reacting said fraction with nitric acid at a temperature within the range of about 130° to about 210° C., wherein the molar ratio of nitric acid to said fraction is in the range of about 3:1 to about 8:1, and thereafter reacting the total resulting reaction product with nitric acid in oleum to obtain a nitration product predominating in dinitrobenzophenones.

17 Claims, No Drawings

PROCESS FOR PREPARING DINITROBENZOPHENONES

BACKGROUND OF THE INVENTION

1. Field of the Invention

The invention defined and claimed herein relates to a process for preparing dinitrobenzophenones which comprises reacting benzene with ethylene in the presence of an alkylation catalyst to obtain an alkylation product containing unreacted benzene, ethylbenzene, polyethylbenzenes, 1,1-diphenylethane and heavier products, separating benzene, ethylbenzene and polyethylbenzenes from said alkylation product, recovering from the remainder of said alkylation product a fraction whose boiling points fall within the temperature range of about 260° to about 290° C., reacting said fraction with nitric acid at a temperature within the range of about 130° to about 210° C., wherein the molar ratio of nitric acid to said fraction is in the range of about 3:1 to about 8:1, and thereafter reacting the total resulting reaction product with nitric acid in oleum to obtain a nitration product predominating in dinitrobenzophenones.

2. Description of Prior Art 1,1-Diphenylethane (DPE) is a valuable hydrocarbon for conversion to benzophenone, which, in turn, can be converted to the corresponding nitro and amine derivatives. Unfortunately, there are no simple methods known for its preparation in high yield. Thus, Baeyer, Ber., VI, 223 (1873) attempted to prepare 1,1-diphenylethane by reacting paraldehyde with benzene in the presence of sulfuric acid, but obtained only a resinous material. Later, in Ber. VII, 1190 (1874), he isolated some 1,1-diphenylethane from a tarry reaction product in disappointingly low yield. Spilker et al., Ber., 65B, 1686 (1932), condensed benzene with styrene in the presence of sulfuric acid and obtained a 25 percent yield of 1,1-diphenylethane. Higher yields of the same product, from 40 to 50 percent, were obtained by Reichert et al., J. Am. Chem. Soc., 45, 3090 (1923) in the mercury-catalyzed condensation of benzene with acetylene in sulfuric acid. More recently, Baeyer et al. in Ber., 94, 1717 (1961) and Ber., 95, 1989, (1962), reacted benzene with acetylene in the presence of phosphoric acid which has been saturated with boron trifluoride to obtain 1,1-diphenylethane in 65 percent yield, as well as some polymeric substances.

It is known that the residue resulting from the alkylation of benzene with ethylene in the presence of an alkylation catalyst, which is available at fuel value from styrene manufacturers, contains substantial amounts of 1,1-diphenylethane. Unfortunately, because of the many compounds associated with the 1,1-diphenylethane in said residue, whose boiling points are close to 1,1-diphenylethane, even efficient fractional distillation of said residue results in a fraction containing only up to about 95 weight percent 1,1-diphenylethane. Because the remaining compounds in said fraction would then function as impurities, the use of said fraction as a 1,1-diphenylethane source for subsequent use would not suggest itself.

J. G. Schulz and A. Onopchenko have shown, however, in their Application Ser. No. 394,260, filed July 1, 1982, entitled Process for Preparing Benzophenone, and assigned to the same assignee as the present invention herein, that by subjecting the defined fraction to oxidation with nitric acid under well defined conditions of reaction they were able to obtain an oxidation product from which by distillation they were able to recover substantially pure benzophenone.

BRIEF DESCRIPTION OF THE INVENTION

The reaction product obtained by J. G. Schulz and A. Onopchenko in the application identified above contains not only the desired benzophenone but also appreciable amounts of 1,1-diphenyl-2-nitroethylene, 1,1-diphenyl-2,2-nitroethylene and other unknown materials. We have found that we can subject the entire reaction product containing the benzophenone obtained by J. G. Schulz and A. Onopchenko to specific nitration conditions and obtain a product containing dinitrobenzophenones, primarily m,m'-dinitrobenzophenone. The amount of dinitrobenzophenones obtained when the entire reaction product of J. G. Schulz and A. Onopchenko are in excess of the amounts that would have been predicted had an equivalent amount of pure benzophenone been subjected to the same nitration reaction. In addition, because the entire reaction product of J. G. Schulz and A. Onopchenko is subjected to nitration rather than the pure benzophenone recovered therefrom, it can be seen that costly recovery processes, for example, distillation, to obtain pure benzophenone from the reaction product of J. G. Schulz and A. Onopchenko are clearly avoided.

The process employed in obtaining the fraction charge used herein is described, in part, in U.S. Pat. No. 4,111,824 of Schulz et al. Thus, the alkylation of benzene with ethylene to obtain the fraction charge that is subjected to nitric acid oxidation, as will be defined hereinafter, can be any of the processes known in the art for producing a product containing ethylbenzene, for example, either liquid phase alkylation or vapor phase alkylation. The molar ratios of benzene to ethylene employed can be, for example, in the range of about 25:1 to about 2:1, preferably about 10:1 to about 3:1. In the liquid phase reaction, for example, the benzene and ethylene, together with an alkylation catalyst, for example, a Friedel Crafts catalyst, such as aluminum chloride or aluminum bromide or some other organo-aluminum halide; Lewis acids, such as promoted $ZnCl_2$, $FeCl_3$ and $BF_3$; and Bronsted acids, including sulfuric acid, sulfonic acid and p-toluene sulfonic acid, hydrofluoric acid, etc., in an amount corresponding to about 0.002 to about 0.050 parts, preferably about 0.005 to about 0.030 parts, relative to ethylbenzene produced, are reacted in a temperature range of about 20° to about 175° C., preferably about 90° to about 150° C., and a pressure in the range of about atmospheric to about 250 psig (about atmospheric to about 1.7 MPa), preferably about 7 to about 200 psig (about 0.05 to about 1.4 MPa) for about 10 minutes to about 10 hours, preferably for about 20 minutes to about 3 hours. In the vapor phase, for example, the reactants can be passed over a suitable alkylation catalyst bed containing alkylation catalysts, such as phosphoric acid on kieselguhr, silica or alumina, aluminum silicates, etc., at a convenient hourly space velocity in a temperature range of about 250° to about 450° C., preferably about 300° to about 400° C., and a pressure of about 400 to about 1200 psig (about 2.7 to about 8.2 MPa), preferably about 600 to about 1000 psig (about 4.1 to about 6.8 MPa).

As a result of such reactions, an alkylation product is obtained containing unreacted benzene, ethylbenzene, polyethylbenzenes, such as diethylbenzene and triethylbenzene, and higher-boiling products.

The alkylation product can be treated in any conventional manner to remove any alkylation catalyst present therein. For example, when aluminum chloride is used as catalyst, the alkylation product can be sent to a settler wherein the aluminum chloride complex is removed and recycled to the reaction zone and the remaining product can then be water-washed and neutralized.

The resulting alkylation product is then distilled at atmospheric pressure or under vacuum to recover unreacted benzene (B.P. 80° C.), ethylbenzene (B.P. 136° C.) and polyethylbenzenes (B.P. 176°–250° C.).

The heavier product remaining after removal of benzene, ethylbenzene and polyethylbenzenes, as described above, is a dark, viscous, high-boiling material from which the fraction charge that is to be subjected to nitric acid oxidation is obtained. The fraction charge is obtained by subjecting the heavier product, defined above, to distillation to recover a fraction whose boiling points at atmospheric pressure (14.7 psig, or 760 mm of mercury) fall within the temperature range of about 260° to about 290° C., preferably about 265° to about 280° C. The amount of 1,1-diphenylethane in the broad fraction will range from about 50 to about 80 weight percent, but in the narrow fraction will range from about 80 to about 95 weight percent.

The fraction so recovered is then subjected to reaction with nitric acid to convert the 1,1-diphenylethane therein to benzophenone following the procedure defined and claimed in U.S. patent application Ser. No. 394,260, filed July 1, 1982 of J. G. Schulz and A. Onopchenko referred to above. In order to obtain high yields of benzophenone, it is critical that the molar ratio of nitric acid (as 100 percent nitric acid) to the fraction charge be in the range of about 3:1 to about 8:1, preferably about 3.5:1 to about 6.5:1. The molar ratio of nitric acid (as 100 percent nitric acid) to 1,1-diphenylethane in the fraction charge required, as shown in our copending application referred to above, is in the range of about 2:1 to about 6:1, preferably about 2.5:1 to about 4.5:1. The excess nitric acid used herein is consumed in the oxidation of the other components associated with 1,1-diphenylethane in the fraction being oxidized. The nitric acid can be an aqueous nitric acid having a concentration of about five to about 90 weight percent, preferably about 10 to about 70 weight percent.

The reaction is simply effected by bringing together the fraction charge into contact with the nitric acid while stirring, while maintaining a temperature of about 130° to about 210° C., preferably about 150° to about 180° C. Pressures are not significant and can be, for example, in the range of about 10 to about 600 psig (0.07 to 4.1 MPa), or even higher, preferably about 50 to about 300 psig (0.3 to 2.1 MPa). A reaction time of about 0.25 to about ten hours, preferably about 0.5 to about six hours, is sufficient. If desired, a catalyst known to be effective in facilitating oxidation reactions, such as cupric oxide, cuprous oxide, vanadium pentoxide, in an amount corresponding to about 0.1 to about 10 weight percent, based on the fraction charge, can be used.

The total oxidation product obtained above is then subjected to nitration with nitric acid in oleum to convert the benzophenone in said nitration product primarily to m,m'-dinitrobenzophenone following the procedure outlined in our U.S. patent application Ser. No. 242,691, filed Mar. 11, 1981 now U.S. Pat. No. 4,361,704 for Process for Preparing m,m'-Dinitrobenzophenone.

Thus, in carrying out the nitration reaction herein, the weight ratio of the total reaction product, sulfuric acid (a 100 percent sulfuric acid) and sulfur trioxide must be in the range of about 1:3:1 to about 1:25:5, but preferably in the range of about 1:2:2 to about 1:15:4. The sulfuric acid and sulfur trioxide employed can be satisfied by the use of oleum. By "oleum" we mean to include concentrated sulfuric acid containing sulfur trioxide. The amount of sulfur trioxide on a weight basis relative to the total weight of sulfuric acid and sulfur trioxide, will be in the range to satisfy the defined weight ratios set forth above, for example, in the range of about five to about 65 weight percent, preferably about 10 to about 35 weight percent. Oleum suitable for use herein can be prepared, for example, by adding gaseous or liquid $SO_3$ to concentrated sulfuric acid. It is believed that sulfur trioxide when dissolved in, or added to, sulfuric acid readily forms $H_2S_2O_7$ and higher polysulfuric acids (R. Gillespie, *J. Chem. Soc.*, 2493 (1950)).

In carrying out the nitration reaction herein, the total oxidation product containing benzophenone, nitric acid, sulfuric acid and sulfur trioxide are brought together, with the weight ratios of each being within the ranges defined above. The amount of nitric acid is not critical and should be sufficient, stoichiometrically, to place one nitro group on each of the rings of the benzophenone being treated. To assure substantially complete reaction, amounts in excess of those required stoichiometrically to obtain dinitrobenzophenones can be used, for example, up to about 10 weight percent, or even higher. The concentration of the nitric acid used can vary over a wide range, for example, from about 50 to about 100 weight percent aqueous nitric acid, preferably from about 67 to about 95 weight percent aqueous nitric acid.

The reaction can be carried out, for example, by stirring the reaction mixture while heating the same in a temperature range of about 5° to about 120° C., preferably about 10° to about 90° C., for about 10 minutes to about 120 hours, or even longer, preferably for about one-half to about 24 hours. In a preferred embodiment in order to further control the reaction to assure obtaining the desired isometric distribution, that is, with a predominance of m,m'-dinitrobenzophenone, the process is carried out in a plurality of stages. In a first stage, for example, the temperature is maintained in a range of about 5° to about 50° C., preferably about 10° to about 30° C., for about 10 minutes to about 10 hours, preferably for about one-half to about eight hours. In a second stage the reaction mixture is maintained in the temperature range of about 20° to about 120° C., preferably about 50° to about 90° C., for about one-half to about five hours, preferably about one to about three hours. The pressure is not critical, and elevated pressures up to about 100 psig (about 0.7 MPa), or even higher, can be used, although atmospheric, or ambient, pressure is preferred.

The dinitrobenzophenones can be recovered from the reaction mixture in any suitable or convenient manner. For example, the reaction mixture can be poured over ice and the resulting slurry can be subjected to filtration. The resulting filter cake, comprising the isomeric mixture of dinitrobenzophenones, can be washed with an alkaline solution, such as sodium hydroxide, potassium hydroxide or ammonium hydroxide, and water, to remove possible contaminating materials therefrom, such as residual nitric acid, sulfuric acid, sulfur trioxide, organic acids, phenolics, etc., and dried. The filter cake will contain substantially high amounts of metadinitrobenzophenones, particularly m,m'-dinitrobenzophenones. The weight ratio of m,m'- to m,p'-dinitrobenzophenones will be in the range of about 90:10 to about 96:4, generally about 92:8 to about 94:6. The filter cake will contain no appreciable amounts of o,o'- or p,p'-dinitrobenzophenones. The weight percent of o,m'-dinitrobenzophenone will be substantially reduced and will amount, for example, to about 0 to about 15 weight percent, generally in the range of 0 to about five weight percent, of the filter cake, but, most preferably, about 0 to about two.

DESCRIPTION OF PREFERRED EMBODIMENTS

The following illustrate the advantages of operating in accordance with the process defined and claimed herein.

Example I

Twenty grams of pure benzophenone were dissolved in 100 milliliters of oleum containing concentrated sulfuric acid and 33 weight percent sulfur trioxide while raising the temperature from 25° to 35° C. In a separate step a nitrating mixture was prepared by slowly adding over a period of 30 minutes, while stirring and cooling, 10.2 milliliters of 90 weight percent aqueous nitric acid to 30 milliliters of oleum containing concentrated sulfuric acid and 33 weight percent sulfur trioxide, maintaining a temperature of 10° to 15° C. The nitrating mixture prepared above was then added over a one-half hour period to the dissolved benzophenone while maintaining a temperature of 25° to 35° C. by occasional cooling. When the addition of acids was completed, the resulting mixture was stirred at 35° C. for one-half hour and then heated to 70° to 75° C., at which point the reaction was continued for one hour. After cooling, the reaction mixture was poured over cracked ice-water mixture and filtered. The solids were washed twice with water, twice with 10 weight percent aqueous sodium hydroxide solution, and twice with water, Final wash water was neutral towards the litmus paper. The solids were dried on a porous plate to give 17.8 grams (60 percent yield) of light tan solids. Analysis by high pressure liquid chromatography showed the presence of two dinitrobenzophenone isomers, 93.5 weight percent m,m'-dinitrobenzophenone and 6.5 weight percent m,p'-dinitrobenzophenone.

Example II

A residue was obtained from the product resulting from the reaction of benzene with ethylene as follows:

Benzene and ethylene in a molar ratio of 9:1 were contacted in the liquid phase, while stirring, in a reactor at a temperature of 130° C. and a pressure of 70 psig (0.5 MPa) in the presence of $AlCl_3$ catalyst over a period of 1 hour, which was sufficient to convert all of the ethylene. The $AlCl_3$ complex catalyst was prepared by dissolving $AlCl_3$ in a polyethylbenzene cut from a previous run so that after the addition, the composition of the catalyst complex was as follows:
  31.5 wt % $AlCl_3$,
  7.0 wt % benzene,
  19.3 wt % ethylbenzene,
  29.8 wt % polyalkylated benzenes,
  3.4 wt % 1,1-diphenylethane, and
  9.0 wt % higher boiling components.

The amount of $AlCl_3$ present in the catalyst mixture amounted to 0.0034 parts by weight per one part by weight or ethylbenzene produced. Also present in the catalyst was ethyl chloride promoter in an amount corresponding to 0.0034 parts by weight per one part by weight or ethylbenzene produced to maintain a high catalyst efficiency. Analysis of the alkylation product showed the presence of:
  49.0 wt % benzene,
  32.9 wt % ethylbenzene,
  17.5 wt % of polyalkylated benzenes
    (6.0 wt % diethylbenzene
    2.7 wt % triethylbenzenes,
    2.1 wt % tetraethylbenzenes, and
    6.7 wt % other alkylbenzenes)
  0.1 wt % 1,1-diphenylethane, and
  0.4 wt % residue.

The alkylation product was subjected to distillation to recover unreacted benzene, ethylbenzene and polyalkylated benzenes, and the benzene and polyalkylated benzenes were recycled to the reaction zone. The residue remaining was a dark, viscous, high-boiling material, and was produced in an amount corresponding to 0.014 parts for each part of ethylbenzene produced.

The residue obtained above was subjected to a vacuum distillatiion, and a fraction was recovered having a boiling point of 82° C. at about 0.5 mm of mercury (270° C. at atmospheric pressure) containing 92.4 weight percent 1,1-diphenylethane. A total of 500 grams of the recovered fraction and 1500 grams of water were charged into a one-gallon autoclave. The autoclave was heated to 150° C. and the pressure regulator was set to maintain a pressure at the level of 250 psig (1.7 MPa). Over a period of two hours there was added to the contents of the autoclave 980 grams of 67 percent aqueous nitric acid. The molar ratio of nitric acid, as 100 percent nitric acid, to the fraction being treated amounted to about 3.8:1. When the acid addition was complete, the reaction was allowed to proceed for one hour. The autoclave was then cooled, depressured and the contents thereof were discharged into a holding tank. After the contents were left standing for one-half hour, the organic layer settled to the bottom, and most of the aqueous phase was decanted. The remaining product was dissolved in about 1800 milliliters of mixed xylenes and was washed twice with 10 percent aqueous sodium hydroxide solutions to dissolve and remove the suspended, xylene-insoluble arylcarboxylic acids. The organic layer was then washed twice with water, dried over anhydrous magnesium sulfate, filtered, and the xylenes were removed in a rotary evaporator to give 452 grams of reaction product. Analysis of the product by gas liquid chromatography showed the presence of 95.3 weight percent benzophenone, 1.1 weight percent nitroolefin and 3.6 weight percent dinitroolefin.

The total of 80 grams of crude product obtained above was dissolved in 960 milliliters of oleum containing concentrated sulfuric acid and 22.5 weight percent sulfur trioxide while maintaining a temperature of 15° to 20° C. This solution was then nitrated with a mixture of 44 milliliters of 90 percent aqueous nitric acid and 122 milliliters of oleum containing concentrated sulfulric acid containing 22.5 weight percent sulfur trioxide at a temperature of 10° to 20° C. After reacting for one hour at 25° C. and then for one hour at 75° C., the reaction mixture was worked out as in Example I. A total of 72 grams of tan solids were isolated (63.0 percent yield). Analysis by high pressure liquid chromatography showed the presence of two dinitrobenzophenone isomers, 93.1 weight percent m,m'-dinitrobenzophenone and 6.9 weight percent m,p'-dinitrobenzophenone.

The results obtained in Example II are surprising. In Example I, 20 grams of benzophenone resulted in 17.8 grams of dinitrobenzophenones. In Example II, the total charge of 80 grams contained 95.3 weight percent benzophenone (76.2 grams), 1.1 weight percent nitroolefin (0.88 grams) and 3.6 weight percent dinitroolefin (2.88 grams). It was believed that the nitroolefinic impurities in Example II would adversely affect the course of the desired reaction. On the basis that if 20 grams of pure benzophenone gave 17.8 grams of dinitrobenzophenones in Example I, it would have been expected that in Example II 76.2 grams of benzophenones in association with the dinitroolefinic impurities would have resulted in less than about 67.8 grams of dinitrobenzophenones (20.0/17.8=76.2/x). And yet, surprisingly, the yield of dinitrobenzophenones in Example II of 63 percent was higher than the yield of dinitrobenzophenones in Example I of 60 percent. The amount of dinitrobenzophenones obtained in Example II, 72 grams, was higher than the 67.8 grams that would have been predicted. Accordingly, not only are the costs and problems associated with the recovery of pure benzophenone from the crude product avoided, prior to nitration, but it would appear desirable, insofar as yields are concerned, to use the entire crude benzophenone product in nitration reaction.

A suitable utilization of the dinitrobenzophenones, particularly the m,m'-dinitrobenzophenone, produced above, are as precursors for the production of the corresponding diaminobenzophenones which are then reacted with benzophenone tetracarboxylic dianhydride (BTDA) to obtain polyimide polymers. The dinitrobenzophenones can be converted to the corresponding diaminobenzophenones by hydrogenation. Here, too, one would normally expect to subject the nitration product obtained above to purification procedures, for example, distillation or recrystallization to recover the desired dinitrobenzophenones prior to hydrogenation. As before, it would be desirable to avoid recovery of the desired dinitrobenzophenones prior to hydrogenation and, instead, subject the entire nitration product to hydrogenation to convert the dinitrobenzophenones therein to the respective diaminobenzophenones.

However, the prior art would lead one to believe that this could not be done because of the possible presence of the dinitroolefins that had been formed during the oxidation of the alkylation bottoms fraction. Thus, Anschutz et al., *Ber.*, 54 B, 1854 (1921), and *Chem. Abstr.*, 16, 903 (1922) point out that chemical reduction of 1,1-diphenyl-2,2-dinitroethylene with stannous chloride and alcoholic hydrogen chloride gives largely diphenylacetonitrile. There is always the danger that if some of the nitrile formed would be further reduced to a primary amine it would act as a chain stopper in the polymerization of the diaminobenzophenones in the polymerization with BTDA. Perhaps more serious is the report of Kohler et al., *J. Am. Chem. Soc.*, 45, 1281 (1923), that in their attempts to hydrogenate the same dinitroolefin, all catalysts used (palladium, platinum and nickel) were poisoned so rapidly that the volume of hydrogen taken up was insignificant. Some of the products identified were bimolecular reduction products, such as tetraphenylsuccinonitriles. And yet, as Example III below shows, hydrogenation of the total product of Example II resulted in effective conversion of dinitrobenzophenone to diaminobenzophenone without any apparent deactivation of catalyst, and as Example IV below shows, the diaminobenzophenone was reacted with BTDA to produce a polyimide resin of satisfactory viscosity.

In our experience, an attempt to hydrogenate pure dinitrobenzophenone in the presence of 2.9 weight percent of dinitroolefin caused the hydrogenation catalyst, palladium on carbon, to be poisoned after less than 10 percent of the theoretical amount of hydrogen had been consumed. Hence, we confirmed the report of Kohler et al., *J. Am. Chem. Soc.*, 45, 1281 (1923) that dinitroolefin in question is a powerful catalyst poison. This is shown below in Example V. It would appear, therefore, that impurities present in the crude benzophenone stream, such as nitroolefin and dinitroolefin, must have been somehow degraded or perhaps converted to dinitrobenzophenones during the nitration reaction in fuming sulfuric acid.

Example III

A total of 20 grams of the total product from Example II, 1.9 grams of a catalyst consisting of 10 weight percent palladium on carbon (having a moisture content of 50 weight percent) was hydrogenated in a Parr shaker in 100 grams of tetrahydrofuran at a temperature of 40° C. and a hydrogen pressure of 50 psig (0.35 MPa) until the theoretical amount of hydrogen was taken up. The resulting product was filtered under nitrogen, the filtrate was concentrated on a rotary evaporator to about one-third its original volume, and diluted with an equal volume of water. The pale yellow flakes that precipitated out of solution were recovered by filtration and dried in a vacuum oven at a temperature of 50° C. over a period of 72 hours to give 10.7 grams of pure m,m'-diaminobenzophenone (melting point 144° to 145° C.), corresponding to a yield of 67 percent. The filtrate contained some additional product, and some product also adhered to the catalyst, but these were not further examined. It would appear that the dinitroolefin impurity that had been present in the crude benzophenone product must have been fortuitously removed or degraded during the nitration step.

Example IV

To determine whether or not the diamine product obtained in Example III is of polymer grade, it was reacted with BTDA as follows: A total of 2.5 grams of the diaminobenzophenone recovered in Example III was added to 30 grams of a mixture containing equal amounts of diglyme and tetrahydrofuran, purged with nitrogen, and, while stirring, 3.8 grams of BTDA were incrementally added over a period of 30 minutes. The initial suspension of the diamine in the solvent finally dissolved when BTDA was added. During the reaction a mild exotherm was evident, as the temperature rose from 22° to 35° C. After the reaction had lined out at 29°-30° C., the reaction was continued for three hours. A sample taken at the end of three hours showed the intrinsic viscosity of the solution to be 0.6 dl/g, indicating that polymer formation had taken place. That an intrinsic viscosity of 0.6 dl/g is a satisfactory value is apparent from Bulletin N74-19772, distributed by National Technical Information Service, U.S. Dept. of Commerce, 5285 Port Royal Road, Springfield, Va. 22151, page 8, wherein it was shown that the reaction of BTDA with m,m'-diaminobenzophenone resulted in a resin having an intrinsic viscosity of 0.55 dl/g.

Example V

The run of Example III was repeated, but using only five grams of pure m,m'-dinitrobenzophenone and 0.16 gram of 2,2-dinitro-1,1-diphenylethylene. The reaction stopped completely after a take-up of only nine percent of the theoretical amount of hydrogen during the first 15 minutes. No hydrogen uptake during the next 45 minutes was noted. This therefore confirms the report of Kohler et al. that the dinitroolefin is a hydrogenation catalyst poison.

Obviously, many modifications and variations of the invention, as hereinabove set forth, can be made without departing from the spirit and scope thereof, and therefore only such limitations should be imposed as are indicated in the appended claims.

We claim:

1. A process for preparing dinitrobenzophenones which comprises reacting benzene with ethylene in the presence of an alkylation catalyst to obtain an alkylation product containing unreacted benzene, ethylbenzene, polyethylbenzenes, 1,1-diphenylethane and heavier products, separating benzene, ethylbenzene and polyethylbenzenes from said alkylation product, recovering from the remainder of said alkylation product a fraction whose boiling points fall within the temperature range of about 260° to about 290° C., reacting said fraction with nitric acid at a temperature within the range of about 130° to about 210° C., wherein the molar ratio of nitric acid to said fraction is in the range of about 3:1 to about 8:1, and thereafter reacting the total resulting reaction product with nitric acid in oleum to obtain a nitration product predominating in dinitrobenzophenones.

2. The process of claim 1 wherein said alkylation catalyst is $AlCl_3$.

3. The process of claim 1 wherein said benzene and said ethylene is reacted in the presence of $AlCl_3$ in a temperature range of about 20° to about 175° C.

4. The process of claim 1 wherein said benzene and said ethylene is reacted in the presence of $AlCl_3$ in a temperature range of about 90° to about 150° C.

5. The process of claim 1 wherein said fraction recovered from said remainder of said alkylation product has boiling points that fall within the temperature ranges of about 265° to about 280° C.

6. The process of claim 1 wherein said recovered fraction is reacted with nitric acid at a temperature within the range of about 150° to about 180° C.

7. The process of claim 1 wherein the molar ratio of said nitric acid to said recovered fraction is in the range of about 3.5:1 to about 6.5:1.

8. The process of claim 1 wherein said total resulting reaction product is reacted with nitric acid in oleum wherein the weight ratios of said total resulting reaction product, sulfuric acid and sulfur trioxide are in the range of about 1:3:1 to about 1:25:5.

9. The process of claim 1 wherein said total resulting reaction product is reacted with nitric acid in oleum wherein the weight ratios of said total resulting reaction product, sulfuric acid and sulfur trioxide are in the range of about 1:2:2 to about 1:15:4.

10. The process of claim 1 wherein said oleum comprises a mixture of sulfuric acid and sulfur trioxide wherein the weight percent sulfur trioxide therein is in the range of about five to about 65 percent.

11. The process of claim 1 wherein said oleum comprises a mixture of sulfuric acid and sulfur trioxide wherein the weight percent sulfur trioxide therein is in the range of about 10 to about 35 percent.

12. The process of claim 1 wherein said nitration is carried out in a temperature range of about 5° to about 120° C. for about 10 minutes to about 120 hours.

13. The process of claim 1 wherein said nitration is carried out in a temperature range of about 10° to about 90° C. for about one-half to about 24 hours.

14. The process of claim 1 wherein said nitration is carried out in at least two stages, in the first of which at a temperature of about 5° to about 50° C. for about 10 minutes to about 10 hours, and in a second stage at a temperature of about 20° to about 120° C. for about one-half to about five hours.

15. The process of claim 1 wherein said nitration is carried out in at least two stages, in the first of which at a temperature of about 10° to about 30° C. for about one-half to about eight hours, and in a second stage at a temperature of about 50° to about 90° C. for about one to about three hours.

16. The process of claim 1 wherein at the end of the reaction the reaction mixture contains in excess of about four weight percent sulfur trioxide.

17. The process of claim 1 wherein at the end of the reaction the reaction mixture contains from about 10 to about 15 weight percent sulfur trioxide.

* * * * *